United States Patent
Nanami et al.

(10) Patent No.: US 6,603,555 B1
(45) Date of Patent: Aug. 5, 2003

(54) GAS DETECTING APPARATUS USING LASER ABSORPTION SPECTROSCOPY

(75) Inventors: Masaya Nanami, Zama (JP); Toshiyuki Suzuki, Atsugi (JP); Takeshi Tsukamoto, Hadano (JP)

(73) Assignee: Anritsu Corporation, Tokyo (JP)

( * ) Notice: Subject to any disclaimer, the term of this patent is extended or adjusted under 35 U.S.C. 154(b) by 0 days.

(21) Appl. No.: 09/478,828

(22) Filed: Jan. 6, 2000

(30) Foreign Application Priority Data

Jan. 19, 1999 (JP) .......................................... 11-011171

(51) Int. Cl.$^7$ .............................................. G01N 21/61
(52) U.S. Cl. ....................................... 356/437; 356/236
(58) Field of Search ................................ 356/437, 438, 356/439, 236; 250/228

(56) References Cited

U.S. PATENT DOCUMENTS

| | | | |
|---|---|---|---|
| 3,319,071 A | * 5/1967 | Werth | 356/236 |
| 3,524,066 A | 8/1970 | Blakkan | |
| 3,562,524 A | * 2/1971 | Moore et al | 250/343 |
| 3,920,336 A | * 11/1975 | Sackett | 356/236 |
| 4,291,988 A | * 9/1981 | Dixon et al. | 356/437 |
| 4,842,404 A | * 6/1989 | Duda | 356/236 |
| 5,047,639 A | 9/1991 | Wong | |
| 5,705,816 A | 1/1998 | Ronge et al. | |

OTHER PUBLICATIONS

V. Nagali et al; "Tunable Diode–Laser Absorption Measurements Of Methane at Elevated Temperatures"; Jul. 20, 1996; pp. 4026–4032; Applied Optics vol. 35, No. 21.
V. Nagali et al: "Tunable Diode–Laser Absorption Measurements of Methane at Elevated Temperatures", Applied Optics, U.S., Society of America, Washington, vol. 35, No. 21, Jul. 20, 1996, pp. 4026–4032, XP000885004, ISSN: 0003–6935; p. 4027, right–hand column, paragraph 3 to p. 4048, left–hand column, paragraph 2, * Figure 2 * .

* cited by examiner

Primary Examiner—Richard A. Rosenberger
(74) Attorney, Agent, or Firm—Frishauf, Holtz, Goodman & Chick, P.C.

(57) ABSTRACT

A gas detecting apparatus includes a gas cell, a laser source, a light diffuser and a photodetector. The gas cell has a gas inlet hole for letting the target gas come inside and a gas discharge hole for discharging the target gas, and retains a target gas to be detected. The laser source emits coherent light into the gas cell in order to detect a concentration of the target gas. The light diffuser is disposed in the optical path of the coherent light output from the laser source to diffuse the coherent light, thereby eliminating coherence of the coherent light. The photodetector receives light diffused by the light diffuser.

12 Claims, 6 Drawing Sheets

GAS DETECTING APPARATUS USING LASER ABSORPTION SPECTROSCOPY

BACKGROUND OF THE INVENTION

The present invention relates to a gas detecting apparatus using laser absorption spectroscopy, and, more particularly, to a gas detecting apparatus having a gas cell which brings about the interaction of a gas to be supplied therein and a laser beam in order to detect the presence or absence of gas as a detection target and measure the concentration of the gas.

It is known that laser absorption spectroscopy is one kind of spectroscopy technology which is used to analyze a target substance using such a property that a substance demonstrates significant absorption with respect to a specific optical wavelength.

Applying this spectroscopy technology in the field of gas analysis can ensure detection of a target gas and measurement of the concentration of that gas.

Figure 9:
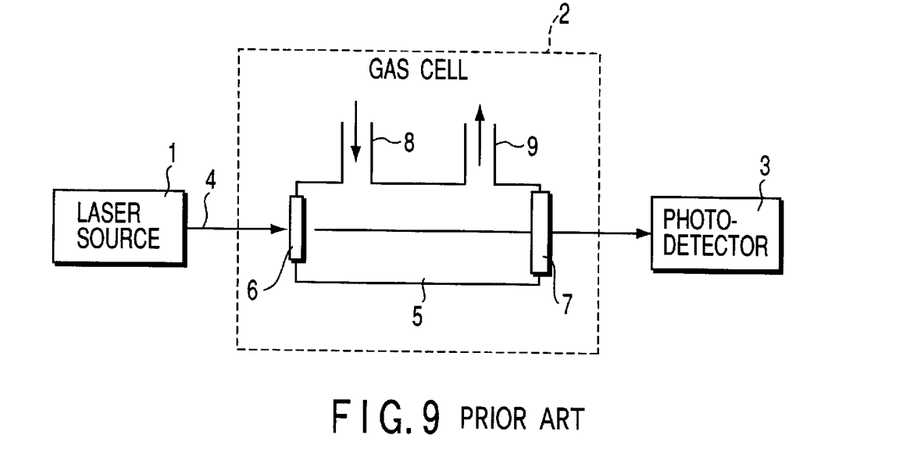
FIG. 9 is a diagram showing the structure of an optical system in a conventional gas detecting apparatus.

FIG. 9 exemplifies an optical system in a conventional gas detecting apparatus.

This optical system comprises a laser source 1, a gas cell 2 where a laser beam 4 from the laser source 1 enters and into which a gas as a detection target is fed, as will be discussed later, and a photodetector 3 which receives the laser beam from this gas cell 2.

The gas cell 2 generally has a container 5 for retaining a gas, a gas inlet hole 8, a gas discharge hole 9, and first and second windows 6 and 7 through which the laser beam 4 passes.

The laser beam 4 emitted from the laser source 1 enters the gas cell 2 through the first window 6, and is then partially absorbed by the gas retained in the container 5, so that the remaining portion of the laser beam 4 emerges from the second window 7 to be received by the photodetector 3.

Figure 10:
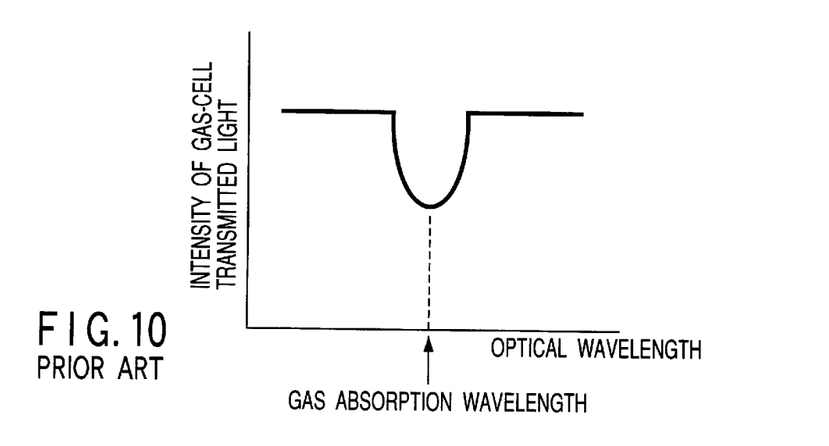
FIG. 10 is a diagram showing a gas absorption characteristic curve for explaining laser absorption spectroscopy.

Spectroscoping the laser beam 4 received by the photodetector 3 by unillustrated spectroscope means, i.e., changing the wavelength of the laser beam 4 in the vicinity of the absorption wavelength of the target gas yields a gas absorption characteristic curve as shown in FIG. 10.

The concentration of the target gas can be detected by measuring the degree of absorption of the laser beam by the gas or the amount of change in the quantity of the laser beam received by the photodetector 3 using a laser beam whose wavelength is as close as possible to the wavelength that shows large absorption on the gas absorption characteristic curve.

When the concentration of a gas is actually measured using the optical system of such a gas detecting apparatus, errors occur due to various factors. Of those errors, the drift-originated error that occurs by the coherence of the laser beam has a large absolute value and is difficult to cope with.

Specifically, when the laser beam 4 passes the windows 6 and 7 of the gas cell 2 or passes through the optical system in the photodetector 3, multiple reflection occurs and the multiple-reflected light component interferes with the original laser beam, so that the result appears as a variation in light intensity.

When this variation in light intensity is superimposed on the absorption curve, it is observed as if the concentration of the target gas were changed.

Figure 11:
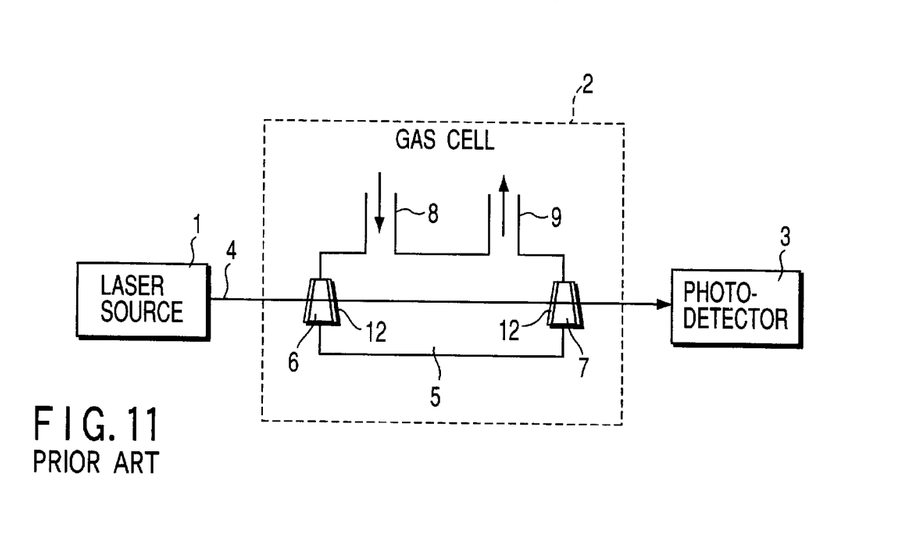
FIG. 11 is a diagram showing the structure of an optical system in a conventional gas detecting apparatus designed to reduce the influence of coherence caused by multiple reflection.

To avoid this optical multiple reflection as much as possible, a countermeasure as shown in FIG. 11 has been taken conventionally (see FIG. 2 and the description lines 15 to 18 of the left column on page 4028, in APPLIED OPTICS/vol. 35, No. 21/20 July 1996, pp. 4026–4032).

In this example, a wedge-like glass plate with a reflection prevention film 12 formed on either side of the glass plate is used for the windows 6 and 7 of the gas cell 2.

This scheme can reduce the influence of the coherence that is caused by the aforementioned multiple reflection.

Even if multiple reflection is suppressed in the gas cell 2 as shown in FIG. 11, a similar problem arises in the photodetector 3 due to coherence of the laser beam.

When a photodiode (hereinafter referred to as "PD") is used as the photodetector 3, for example, multiple reflection occurs between the window of the PD container and the surface of the PD. The multiple-reflected light component leads to a measuring error.

Because a coherence-originated error may occur at various places in the optical system, it is hard to make such an improvement as not to cause coherence in every optical part.

BRIEF SUMMARY OF THE INVENTION

Accordingly, it is an object of the present invention to provide a gas detecting apparatus which utilizes laser absorption spectroscopy and can measure the concentration of a target gas to be detected at a high precision by suppressing a measuring error caused by multiple reflection of a laser beam used in the measurement.

To achieve the above object, a gas detecting apparatus according to one aspect of this invention comprises:

a gas cell for retaining a target gas to be detected, the gas cell having a gas inlet hole for letting the target gas come inside and a gas discharge hole for discharging the target gas;

a laser source for emitting coherent light into the gas cell in order to detect a concentration of the target gas;

light diffusion means, disposed in an optical path of the coherent light output from the laser source, for diffusing the coherent light, thereby eliminating coherence of the coherent light; and a photodetector for receiving light diffused by the light diffusion means.

According to this aspect of the invention, providing the light diffusion means inside or outside the gas cell can reduce optical noise which is originated from coherence.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Reference will now be made in detail to the presently preferred embodiments of the invention as illustrated in the accompanying drawings, in which like reference numerals designate like or corresponding parts.

Outline of the Invention

To begin with, the outline of this invention will be described.

Conventionally, to suppress multiple reflection in the aforementioned gas cell 2 and reduce the influence of coherence caused by multiple reflection at the photodetector 3, the optical path length in a target gas to be detected is set longer to increase the amount of optical absorption by the target gas and the S/N ratio, thereby improving the measuring precision. This requires that the coherence of the light to be used in measurement should be so maintained as not to change the beam size as much as possible.

The present inventors have paid attention to the fact that the aforementioned problem arises because a laser beam has coherence, and have taken an approach, contrary to the conventional one, of allowing the light diffusion means to diffuse the laser beam emitted from the laser source to positively reduce coherence and change the laser beam into incoherent light.

Specifically, a gas detecting apparatus according to this invention comprises a gas cell for retaining a target gas to be detected, the gas cell having a gas inlet hole for letting the target gas come inside and a gas discharge hole for discharging the target gas, a laser source for emitting coherent light into the gas cell in order to detect a concentration of the target gas, light diffusion means, disposed in an optical path of the coherent light output from the laser source, for diffusing the coherent light, thereby eliminating coherence of the coherent light, and a photodetector for receiving light diffused by the light diffusion means.

According to the gas detecting apparatus embodying this invention, as apparent from the above, coherence-originated optical noise can be reduced by providing the light diffusion means in the optical path of the light including the interior or exterior of the gas cell.

Referring to the results of experiments, the following will discuss the function and effects of the light diffusion means which is used in the gas detecting apparatus of this invention.

Figure 12:
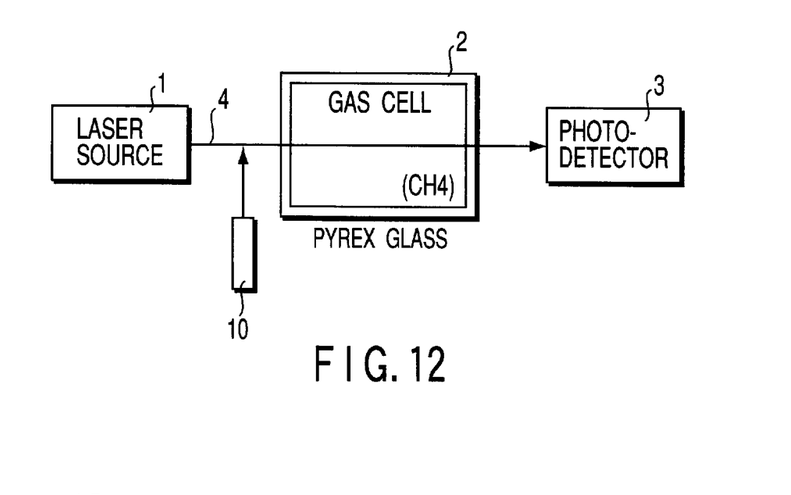
FIG. 12 is a diagram depicting an optical system for measuring a gas absorption characteristic curve for explaining the outline of the gas detecting apparatus of this invention.

FIG. 12 shows a measuring system for observing a gas absorption characteristic curve for explaining the function of the light diffusion means used in the gas detecting apparatus of this invention.

This measuring system comprises a laser source 1, a gas cell 2 where a laser beam 4 from the laser source 1 enters and into which a gas as a detection target is fed, as will be discussed later, a photodetector 3 which receives the laser beam from this gas cell 2, and a light diffuser 10 as light diffusion means which is selectively inserted in the optical path of the laser beam 4.

In this example, the gas cell 2 in use has a cylindrical container (having a length of 2 cm) of Pyrex glass in which 100% methane gas is sealed at $1.33 \times 10^4$ Pa.

Those portions of this gas cell 2 where the laser beam 4 passes are formed flat.

Note that a distributed feedback semiconductor laser (DFB-LD) is used as the laser source 1.

The oscillation wavelength of the laser beam 4 from the laser source 1 is 1653.7 nm has a spectrum line width of approximately 10 MHz.

It is to be noted that the oscillation wavelength of the laser beam 4 from the laser source 1 matches with one of near infrared absorbing lines of a methane gas.

As the light diffuser 10, an acrylate resin plate which has its surface polished into frosted glass by #280 sand paper is used.

The absorption curve for the methane gas is acquired by changing the oscillation wavelength in the vicinity of the gas's absorbing lines while varying the temperature of the DFB-LD used as the laser source 1 and then sequentially plotting the intensity of the laser beam 4 that passes through the gas cell 2.

Figure 13:
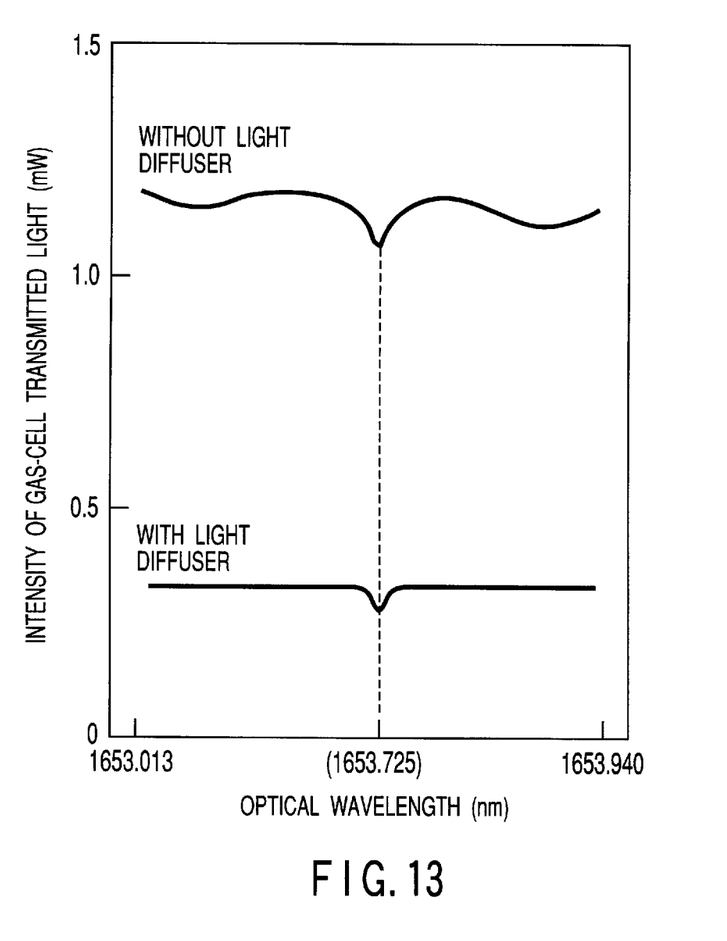
FIG. 13 is a diagram depicting methane-gas absorption curves for explaining the outline of the gas detecting apparatus of this invention.

FIG. 13 shows the difference between methane-gas absorption curves with and without the light diffuser 10 for explaining the function of the light diffusion means used in the gas detecting apparatus of this invention.

In FIG. 13, the horizontal scale represents the wavelength of the laser beam 4, and the vertical scale the intensity of the gas-cell transmitted light.

Of the two absorption curves shown in FIG. 13, the one in a case where the light diffuser 10 is not provided shows a periodic variation in the intensity of the gas-cell transmitted light as the wavelength of the laser beam 4 varies.

This variation in light intensity is caused by the coherence that has been originated from the multiple reflection of the laser beam 4, and has an intensity width equivalent to about 3% absorption in terms of the gas concentration.

Because the inherent gas absorption appears as being superimposed on the variation in light intensity, the gas concentration observed differs depending on whether the absorption curve is superimposed at the crest portion of the periodic change or at the trough portion.

Of the two absorption curves shown in FIG. 13, the other one in a case where the light diffuser 10 is present, unlike the former absorption curve involving no light diffuser, does not shows a periodic variation in the intensity of the gas-cell transmitted light.

That is, it is apparent from the results of this experiment that the light diffuser 10 reduces the coherence of the laser beam 4, making the influence of the multiple-reflection originated coherence smaller.

How much the coherence of the laser beam 4 is decreased by such diffusion of the laser beam 4 can be numerically given by measuring the coherence intensity.

Figure 14:
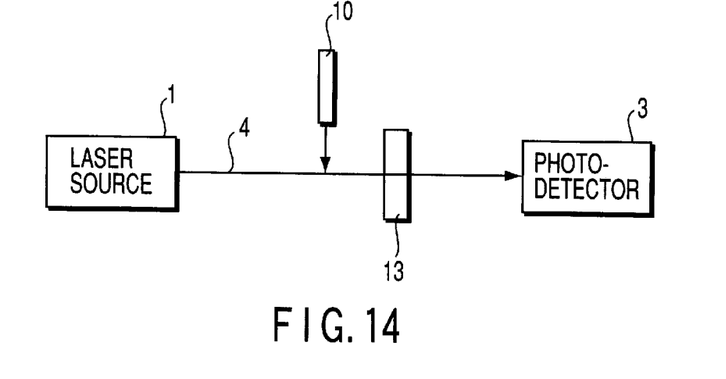
FIG. 14 is a diagram depicting an optical system for measuring the intensity of coherence for explaining the outline of the gas detecting apparatus of this invention.

FIG. 14 shows a measuring system for measuring the coherence intensity for explaining the function of the light diffusion means used in the gas detecting apparatus of this invention.

This measuring system comprises the laser source 1, a plane parallel glass plate 13 where the laser beam 4 from the laser source 1 enters, the photodetector 3 which receives the laser beam from this plane parallel glass plate 13, and the light diffuser 10 which is selectively inserted in the optical path of the laser beam 4 between the laser source 1 and the plane parallel glass plate 13.

First, without the light diffuser 10 inserted on the optical axis between the laser source 1 and the plane parallel glass plate 13, after the optical axis is adjusted in such a way that the laser beam 4 from the laser source 1 can be perpendicularly incident to the plane parallel glass plate 13, the light transmitted through the plane parallel glass plate 13 is received by the photodetector 3 while carrying out wavelength scanning of the laser beam 4, and then the periodic variation in light intensity is observed.

In general, this periodic variation shows a waveform called an etalon transmission characteristic which is determined by the thickness and surface reflectance of the plane parallel glass plate 13.

Next, with the light diffuser 10 inserted on the optical axis between the laser source 1 and the plane parallel glass plate 13, the transmission characteristic of the laser beam 4 is observed.

When the light diffuser 10 is inserted, the phase of the laser beam 4 is disturbed at random so that even if multiple reflection of the laser beam 4 occurs, coherence hardly appears so that a variation in light intensity is small even with wavelength scanning.

The amount of the coherence intensity which has been reduced by the light diffuser 10 can be quantized by measuring the ratio of the change in light intensity to the maximum intensity of the received light from the transmission characteristic acquired by the above-described measuring method.

Figure 15:
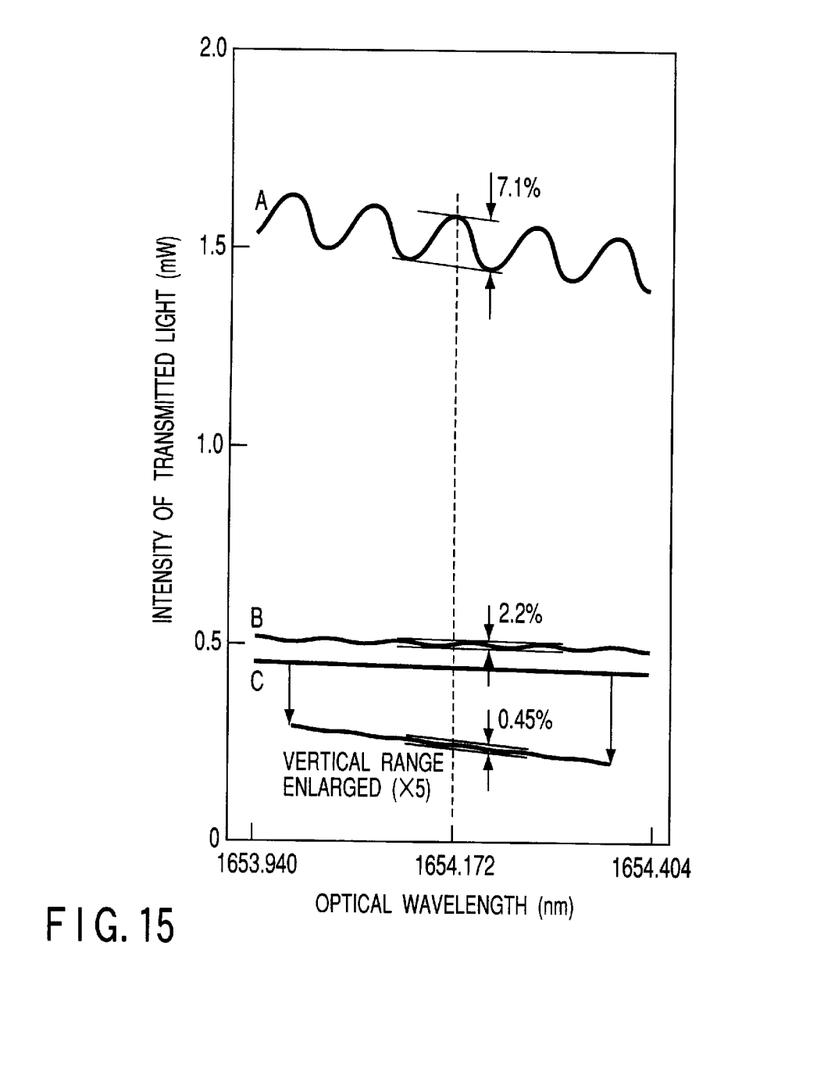
FIG. 15 is a diagram showing the characteristic of the intensity of transmitted light for explaining the outline of the gas detecting apparatus of this invention.

FIG. 15 shows the characteristic of the intensity of light transmitted the plane parallel glass plate 13 in three curves, depending on whether or not the light diffuser 10 is inserted, for explaining the function of the light diffusion means used in the gas detecting apparatus of this invention.

In FIG. 15, the horizontal scale represents the wavelength of the laser beam 4, and the vertical scale the intensity of the light transmitted the plane parallel glass plate 13.

In FIG. 15, "A" shows the characteristic in a case where the laser beam 4 passed only the plane parallel glass plate 13, and "B" and "C" shows the characteristics in a case where the light diffuser 10 was inserted.

For the characteristic C, the vertical range is shown in a 5× magnification.

In this case, acrylate resin plates which have their surfaces polished by #600 sand paper and #280 sand paper are used as the light diffuser 10 in the cases B and C, respectively.

The plane parallel glass plate 13 in use has a thickness of 10 mm.

The three transmission characteristics A, B and C near the optical wavelength of 1654.172 nm shown in FIG. 15 will be compared with one another.

First, for the transmission characteristic A with only the plane parallel glass plate 13, the coherence intensity is 7.1%.

In the case of the transmission characteristic B with the light diffuser 10 whose surface has been polished by the #600 sand paper, the coherence intensity becomes smaller to 2.2%.

For the transmission characteristic C with the light diffuser 10 whose surface has been polished by the #280 sand paper, the coherence intensity becomes smaller to 0.45%.

It is apparent that the light diffusion means effectively works as means for making the coherence intensity smaller.

Although an acrylate resin plate having its surface polished by sand paper is used as the light diffusion means in the above-described experiment, the same effects may be acquired by using optical glass plate processed into a frosted glass like form using a polisher, or metal particles blended into a transparent plastic plate or glass plate, or an optical component sold as a "light diffuser" or "diffuser".

How much the coherence of the laser beam emitted from the laser source should be reduced to make the influence of coherence appear as having become sufficiently smaller would vary depending on how accurate the measurement should be made by reducing an error or drift in measuring the concentration of the target gas.

In a gas detecting apparatus which reads the absorption rate from the absorption peak on the absorption curve to thereby measure the gas concentration, an error or drift resulting from the influence of coherence is proportional to the ratio of the coherence intensity.

When one wants to reduce an error or drift in measuring the gas concentration to a half, the light diffusion means that reduces the coherence intensity to a half should be used.

When one wants to improve an error or drift in measuring the gas concentration by a factor of one digit, the light diffusion means that reduces the coherence intensity by a factor of 10 should be used.

Various embodiments of the gas detecting apparatus according to this invention which are based on the above-outlined principle will be discussed below with reference to the accompanying drawings.

First Embodiment

Figure 1:
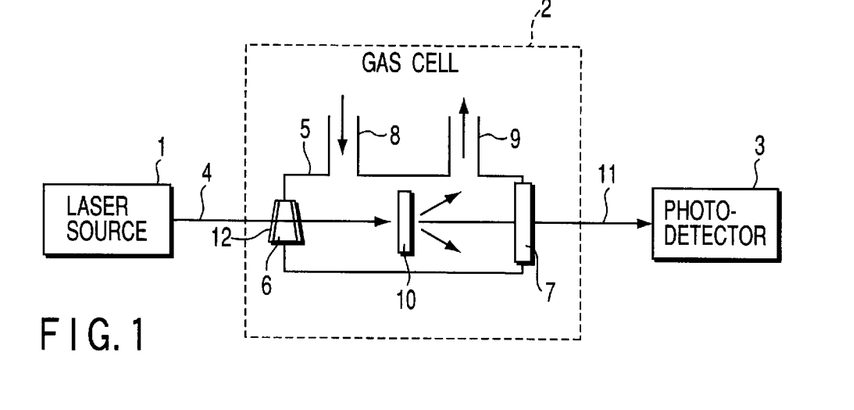
FIG. 1 is a diagram illustrating the structure of an optical system in a gas detecting apparatus according to a first embodiment of this invention.

FIG. 1 is a diagram illustrating the structure of an optical system in a gas detecting apparatus according to a first embodiment of this invention.

The optical system shown in FIG. 1 includes the laser source 1, the gas cell 2 where the laser beam 4 from the laser source 1 enters and into which a gas as a detection target is fed, as will be discussed later, and the photodetector 3 which receives the laser beam from this gas cell 2.

The optical system according to the first embodiment is arranged, as apparent from the above, in such a way that and the laser beam 4 from the laser source 1 passes the gas cell 2 and enters the photodetector 3, and further comprises the light diffuser 10 as light diffusion means which is inserted in the optical path of the laser beam 4.

In this case, a laser whose oscillation wavelength matches with the absorption spectrum of the target gas and which has an optical spectral line width narrow than the absorption spectral line width of the target gas, e.g., the aforementioned distributed feedback semiconductor laser (DFB-LD) is used as the laser source 1.

The gas cell 2 generally has a container 5 for retaining the target gas, a first window 6 which the light beam 4 from the laser source 1 can enter and a second window 7 from which the light beam 4 can emerge.

A contact portion between the container 5 and each of the windows 6 and 7 has an air-tight structure.

Further, the container 5 of the gas cell 2 is provided with a gas inlet hole 8 for letting the target gas inside and a gas discharge hole 9 for discharging the target gas.

A metal such as aluminum or stainless steel, or glass can be used as the material for the container 5 depending on the type of the target gas.

When the target gas is a non-corrosive gas like carbon dioxide ($CO_2$), methane ($CH_4$) or nitrous oxide ($N_2O$), the container 5 of metal is used.

When the target gas is a corrosive gas like ammonia ($NH_3$) or hydrogen chloride (HCl), the container 5 of glass is used.

The light diffuser 10 as the light diffusion means is provided in the container 5 to reduce the coherence of the laser beam 4.

The operation of the thus constituted gas detecting apparatus according to the first embodiment of this invention will be discussed below.

The laser beam 4 from the laser source 1 enters the gas cell 2 and passes through or is reflected at the light diffuser 10 in the gas cell 2 to become diffused light 11 part of which travels toward the photodetector 3.

In this case, a wedge-like optical substrate with a reflection prevention film 12 formed on either side thereof is used for the window 6 of the gas cell 2. This is because the coherence of the laser beam 4 when passing the first window 6 of the gas cell 2 is still large.

The diffused light 11 that passes the second window 7 of the gas cell 2 however has small coherence. Therefore, this window 7 has only to be formed of a material which can pass the diffused light 11 of the laser beam 4 and an inexpensive ordinary glass plate may be used.

As the light diffuser 10 provided in the container 5, an acrylate resin plate which or a glass plate or metal particles blend into a transparent plastic plate or glass plate has its surface polished into slip glass, or an optical component sold as a "light diffuser" or "diffuser" may be used.

According to the gas detecting apparatus of the first embodiment of the invention with the above-described structure, optical noise which is caused by the coherence of the laser beam 4 becomes significantly small, so that the photodetector 3 can detect only a change in the optical intensity caused by the optical absorption of the target gas, thus ensuring stable measurement of the gas concentration.

Second Embodiment

Figure 2:
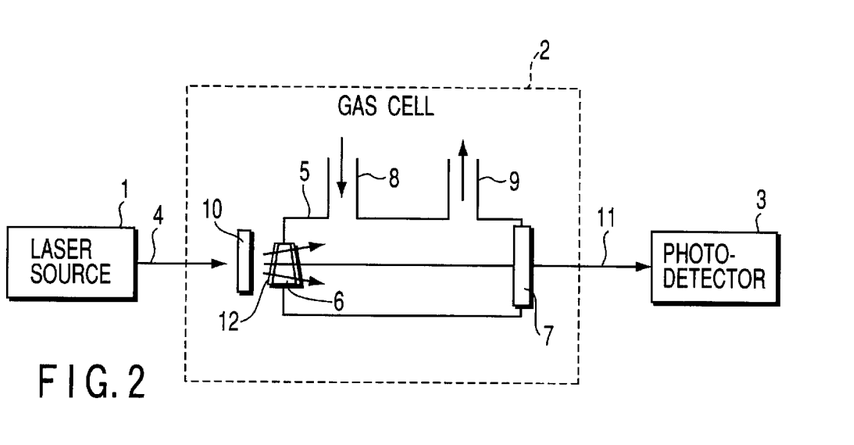
FIG. 2 is a diagram illustrating the structure of an optical system in a gas detecting apparatus according to a second embodiment of this invention.

FIG. 2 illustrates the structure of an optical system in a gas detecting apparatus according to a second embodiment of this invention.

This second embodiment has the same structure as the first embodiment except for the light diffuser 10 located between the laser source 1 and the first window 6.

The second embodiment has such an advantage that the coherence of the laser beam 4 that has passed the light diffuser 10, i.e., the diffused light 11, is reduced so that inexpensive glass plates can be used for both the first and second windows 6 and 7.

Third Embodiment

Figure 3:
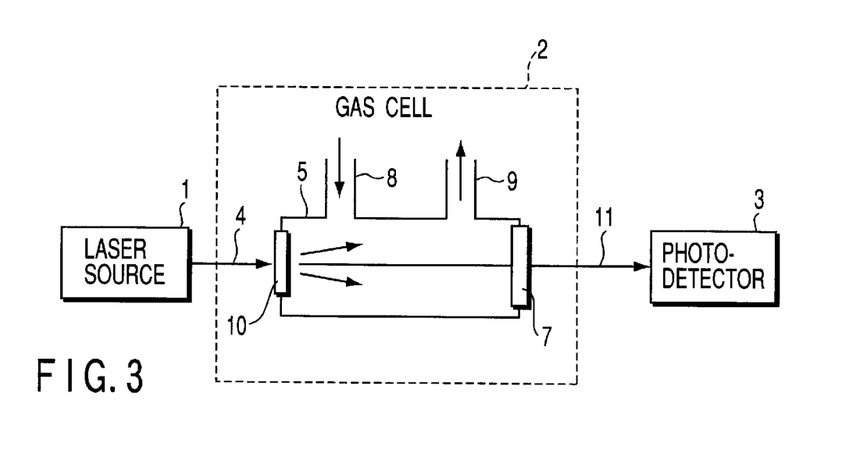
FIG. 3 is a diagram illustrating the structure of an optical system in a gas detecting apparatus according to a third embodiment of this invention.

FIG. 3 illustrates the structure of an optical system in a gas detecting apparatus according to a third embodiment of this invention.

This third embodiment has the same structure as the first embodiment except that the first window 6 is replaced with the light diffuser 10 of a transmission type.

The third embodiment has such an advantage that it is unnecessary to provide light diffusion means in the gas cell 2 and the use of the light diffuser 10 also as the first window 6 can reduce the number of the components of the gas cell 2.

Fourth Embodiment

Figure 4:
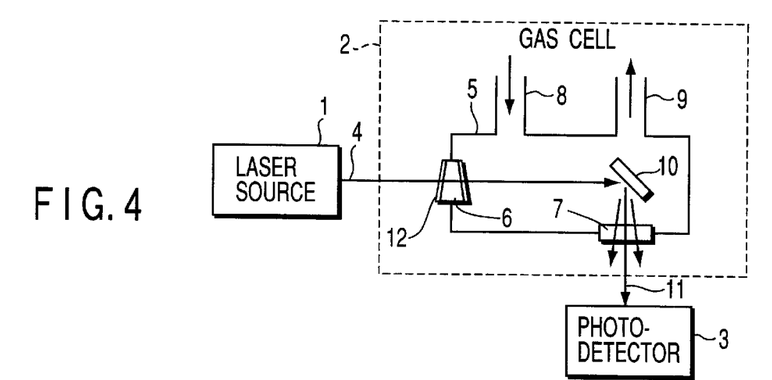
FIG. 4 is a diagram illustrating the structure of an optical system in a gas detecting apparatus according to a fourth embodiment of this invention.

FIG. 4 illustrates the structure of an optical system in a gas detecting apparatus according to a fourth embodiment of this invention.

This fourth embodiment has the same structure as the first embodiment except that the light diffuser 10 used in the first embodiment is changed to a reflection type light diffuser.

In this example, a light diffuser of glass or metal which has frosting-finished surfaces, or which has aluminum or gold vapor-deposited on the frosting-finished surfaces, or which has a powder of a large reflectance (polytetrafluoroethylene, barium sulfate, sulfur) applied to the frosting-finished surfaces can be used as the light diffuser 10.

According to the fourth embodiment, in any of the cases, the light that is reflected at the surface diffuses, lowering the coherence so that stable measurement of the gas concentration is possible.

Fifth Embodiment

Figure 5:
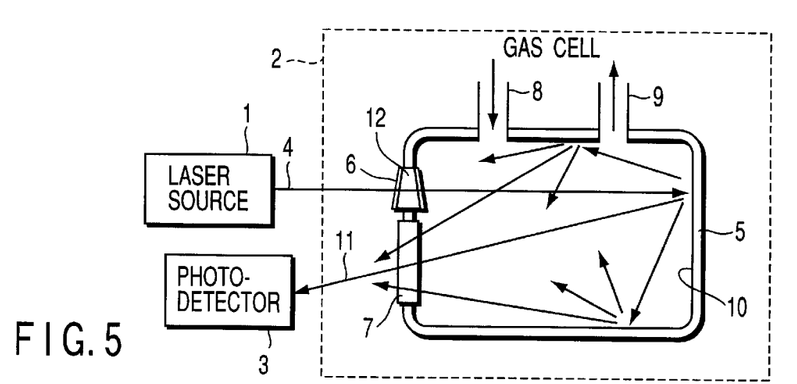
FIG. 5 is a diagram illustrating the structure of an optical system in a gas detecting apparatus according to a fifth embodiment of this invention.

FIG. 5 illustrates the structure of an optical system in a gas detecting apparatus according to a fifth embodiment of this invention.

This fifth embodiment has the same structure as the first embodiment except that the reflection type light diffuser 10 as the light diffusion means is provided on the entire inner surface of the container 5 of the gas cell 2 and the inner wall of the container 5 is so formed as to have no corners.

In this example, the photodetector 3 is provided at a location where light does not enter the photodetector 3 directly.

With this structure of the fifth embodiment, the incident light is reflected multiple times in the container 5 so that lights reach the photodetector 3 through various paths, thus increasing the intensity of the received light which leads to an improved S/N ratio.

The reason why no corners are formed on the inner wall of the container 5 of the gas cell 2 is to prevent attenuation of the amount of light caused by multiple reflection as much as possible.

According to the fifth embodiment with the above structure, the length of the interaction between the target gas and the laser beam 4 becomes longer, increasing the ratio of absorption by the gas, so that the gas concentration can be measured at a higher sensitivity than the structure wherein the laser beam passes the gas cell 2 only once.

Sixth Embodiment

Figure 6:
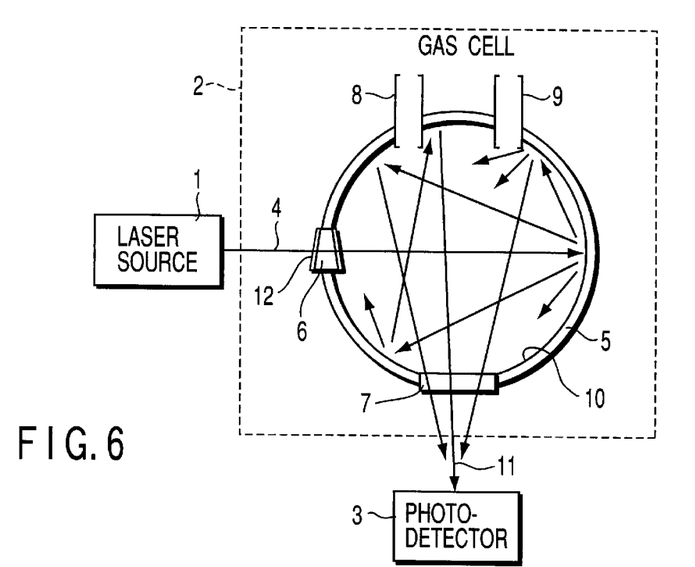
FIG. 6 is a diagram illustrating the structure of an optical system in a gas detecting apparatus according to a sixth embodiment of this invention.

FIG. 6 illustrates the structure of an optical system in a gas detecting apparatus according to a sixth embodiment of this invention.

This sixth embodiment has the same structure as the fifth embodiment except that the container 5 for retaining the target gas has a spherical shape.

In the sixth embodiment, as in the fifth embodiment, the light diffuser 10 is provided on the entire inner surface of the container 5 of the gas cell 2 and the photodetector 3 is provided at a location where light does not enter the photodetector 3 directly.

As the shape of the container 5 of the gas cell 2 is made spherical in the sixth embodiment, the polarization of the optical intensity in the container 5 becomes smaller so that there hardly is a change in optical intensity which depends on the angle of incidence of the laser beam and the installation position of the photodetector 3.

In this case, the spherical container 5 of the gas cell 2 may be formed by using aluminum, brass, glass or the like, subjecting the inner wall of the sphere to honing and then subjecting the resultant inner wall to plating with gold.

This structure of the sixth embodiment brings about such an advantage that a temperature-dependent drift becomes smaller, thus ensuring stable measurement of the gas concentration.

Seventh Embodiment

Figure 7:
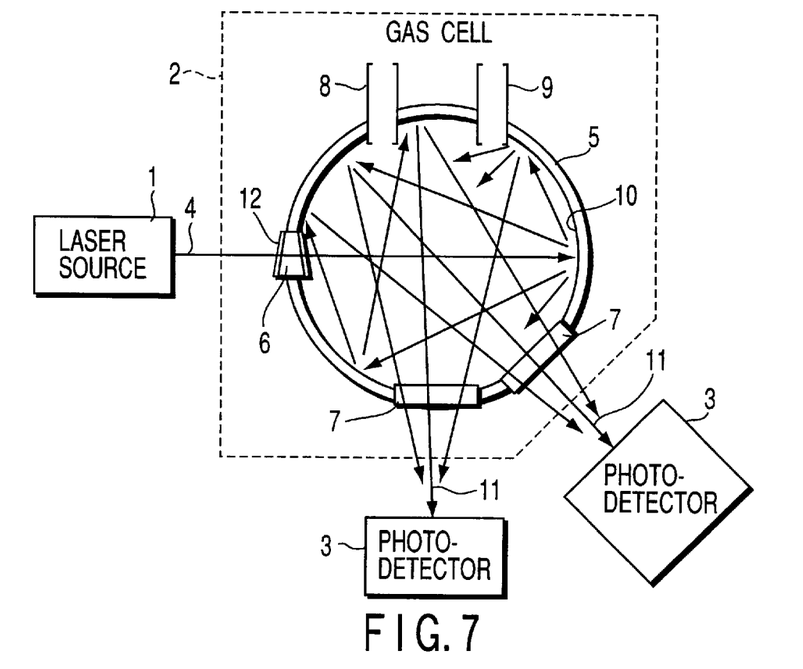
FIG. 7 is a diagram illustrating the structure of an optical system in a gas detecting apparatus according to a seventh embodiment of this invention.

FIG. 7 illustrates the structure of an optical system in a gas detecting apparatus according to a seventh embodiment of this invention.

This seventh embodiment has the same structure as the sixth embodiment except that a plurality of photodetectors 3 (two in this embodiment), the type used in the sixth embodiment, are provided.

The seventh embodiment is advantageous in that the provision of a plurality of photodetectors 3 increases the intensity of the received light, thus improving the S/N ratio and reducing a measuring error caused by the non-uniform gas concentration in the container 5.

Eighth Embodiment

Figure 8:
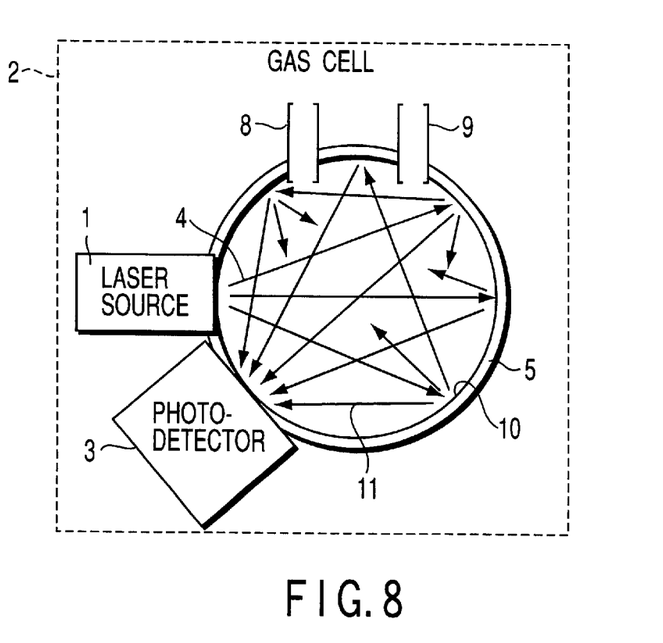
FIG. 8 is a diagram illustrating the structure of an optical system in a gas detecting apparatus according to an eighth embodiment of this invention.

FIG. 8 illustrates the structure of an optical system in a gas detecting apparatus according to an eighth embodiment of this invention.

This eighth embodiment has the same structure as the sixth embodiment except for the laser source 1 and photodetector 3 both installed on the wall of the container 5 of the gas cell 2 which retains the target gas.

In the eighth embodiment, installation of the laser source 1 and photodetector 3 on the wall of the container 5 of the gas cell 2 can eliminate the need for the first and second windows 6 and 7 as used in the first to seventh embodiments.

According to the eighth embodiment, if the laser source 1 is a semiconductor laser (LD), the light diverging from the end face of the LD has only to be irradiated directly into the gas cell 2, which eliminates the need for a component such as a collimator lens or an optical isolator. This can realize an inexpensive optical system.

Further, the eighth embodiment has such an advantage that fine adjustment of the optical axis is hardly necessary, which can significantly reduce the amount of work in manufacturing the optical system as well as makes the optical system less likely to be affected by a change in the ambient environment.

Unlike the conventional gas detecting apparatus that suffers multiple reflection of the laser beam in the optical system including the gas cell, which appears as a change in optical intensity that is a main factor in causing a measuring error, the gas detecting apparatus according to this invention positively reduces the coherence of the laser beam using the light diffusion means, thereby reducing a variation in the light intensity originated from the coherence. This invention can therefore grant stable measurement of the gas concentration while suppressing the measuring error.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A gas detecting apparatus comprising:
    a gas cell for retaining a target gas to be detected, said gas cell having a gas inlet opening for enabling the target gas to enter the gas cell and a gas discharge opening for discharging the target gas;
    a laser source for emitting coherent light into the gas cell in order to detect a concentration of the target gas;
    light diffusion means, disposed in an optical path of the coherent light output from the laser source, for diffusing the coherent light to thereby eliminate coherence of the coherent light; and
    a photodetector for receiving light diffused by the light diffusion means;
    wherein the gas cell includes a container for containing the target gas, a first window through which the light from the laser source can enter, and a second window from which the light from the laser source can emerge;
    wherein a contact portion between the container and each of the first and second windows of the gas cell has an air-tight structure; and
    wherein said light diffusion means comprises a light diffuser arranged between the laser source and the first window of the gas cell.

2. The gas detecting apparatus according to claim 1, wherein the container is made of a material containing one of aluminum, brass, stainless steel and glass in accordance with a type of the target gas.

3. The gas detecting apparatus according to claim 2, wherein when the target gas is a non-corrosive gas including one of carbon dioxide ($CO_2$), methane ($CH_4$) and nitrous oxide ($N_2O$), the container is made of a metal including one of aluminum, brass and stainless steel.

4. The gas detecting apparatus according to claim 2, wherein when the target gas is a corrosive gas including one of ammonia ($NH_3$) and hydrogen chloride (HCl), the container is made glass.

5. The gas detecting apparatus according to claim 1, wherein said light diffuser comprises one of an acrylate resin plate, a glass plate having a surface polished into frosted glass, and a glass or transparent plastic plate having metal particles blended therein.

6. The gas detecting apparatus according to claim 1, wherein said laser source comprises a laser having an oscillation wavelength matching with an absorption spectrum of the target gas and an optical spectral line width narrower than an absorption spectral line width of the target gas.

7. A gas detecting apparatus comprising:

a gas cell for retaining a target gas to be detected, said gas cell having a gas inlet opening for enabling the target gas to enter the gas cell and a gas discharge opening for discharging the target gas;

a laser source for emitting coherent light into the gas cell in order to detect a concentration of the target gas;

light diffusion means, disposed in an optical path of the coherent light output from the laser source, for diffusing the coherent light to thereby eliminate coherence of the coherent light; and a photodetector for receiving light diffused by the light diffusion means;

wherein the gas cell includes a container for containing the target gas, a first window through which the light from the laser source can enter, and a second window from which the light from the laser source can emerge;

wherein a contact portion between the container and each of the first and second windows of the gas cell has an air-tight structure; and wherein said fast window comprises a transmission type light diffuser as said light diffusion means.

8. The gas detecting apparatus according to claim 7, wherein the container is made of a material containing one of aluminum, brass, stainless steel and glass in accordance with a type of the target gas.

9. The gas detecting apparatus according to claim 8, wherein when the target gas is a non-corrosive gas including one of carbon dioxide ($CO_2$), methane ($CH_4$) and nitrous oxide ($N_2O$), the container is made of a metal including one of aluminum, brass and stainless steel.

10. The gas detecting apparatus according to claim 8, wherein when the target gas is a corrosive gas including one of ammonia ($NH_3$) and hydrogen chloride (HCl), the container is made glass.

11. The gas detecting apparatus according to claim 7, wherein said light diffuser comprises one of an acrylate resin plate, a glass plate having a surface polished into frosted glass, and a glass or transparent plastic plate having metal particles blended therein.

12. The gas detecting apparatus according to claim 7, wherein said laser source comprises a laser having an oscillation wavelength matching with an absorption spectrum of the target gas and an optical spectral line width narrower than an absorption spectral line width of the target gas.

* * * * *